(12) United States Patent
Olson et al.

(10) Patent No.: US 10,765,509 B2
(45) Date of Patent: Sep. 8, 2020

(54) INTRAOCULAR DEVICES AND METHODS FOR CORRECTION OF APHAKIA, RESTORATION OF ACCOMMODATION, AND TREATMENT OF GLAUCOMA

(71) Applicant: The Regents of the University of Colorado, a body corporate, Denver, CO (US)

(72) Inventors: Jeffrey Olson, Denver, CO (US); Michael Erlanger, Denver, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 104 days.

(21) Appl. No.: 15/770,067

(22) PCT Filed: Oct. 20, 2016

(86) PCT No.: PCT/US2016/057816
§ 371 (c)(1),
(2) Date: Apr. 20, 2018

(87) PCT Pub. No.: WO2017/070288
PCT Pub. Date: Apr. 27, 2017

(65) Prior Publication Data
US 2018/0311032 A1    Nov. 1, 2018

Related U.S. Application Data

(60) Provisional application No. 62/244,260, filed on Oct. 21, 2015.

(51) Int. Cl.
*A61F 2/16* (2006.01)
*A61F 9/007* (2006.01)
*G02C 7/04* (2006.01)

(52) U.S. Cl.
CPC .............. *A61F 2/1605* (2015.04); *A61F 2/16* (2013.01); *A61F 2/1629* (2013.01);
(Continued)

(58) Field of Classification Search
CPC ... A61F 2002/1681–2002/1683; A61F 2/1648; A61F 2/1694; A61F 2002/169;
(Continued)

(56) References Cited

U.S. PATENT DOCUMENTS 4,073,014 A * 2/1978 Poler .......................... A61F 2/16
                                                                623/6.41
4,387,706 A * 6/1983 Glass ................. A61B 17/0231
                                                                600/208

(Continued)

FOREIGN PATENT DOCUMENTS

| WO | 2014148922 A2 | 9/2014 |
| WO | 2016113634 A1 | 7/2016 |

OTHER PUBLICATIONS

International Preliminary Report on Patentability dated May 3, 2018 in the International Application No. PCT/US2016/057816.
(Continued)

*Primary Examiner* — Paul B Prebilic
(74) *Attorney, Agent, or Firm* — Snell & Wilmer L.L.P.

(57) ABSTRACT

A device according to the present disclosure comprises an intraocular prosthetic. In some embodiments, the device comprises a lens portion and a plurality of arms that radiate outward from the lens portion. The lens portion can comprise a central ring used to hold an intraocular lens. Each arm can comprise a foot plate which allows the device to push out distally against a ciliary body. Among other things, an intraocular device according to the present disclosure can be useful in correction of aphakia, restoration of accommodation, and treatment of glaucoma.

17 Claims, 10 Drawing Sheets

(52) U.S. Cl.
CPC .......... *A61F 9/00781* (2013.01); *G02C 7/04* (2013.01); *A61F 2002/1682* (2015.04); *A61F 2002/1689* (2013.01); *A61F 2220/0091* (2013.01); *A61F 2250/0067* (2013.01); *A61F 2250/0098* (2013.01)

(58) Field of Classification Search
CPC .. A61F 2002/16901; A61F 2002/16902; A61F 2/1605; A61F 2/1629; A61F 2220/0008; A61F 2230/0065; A61F 2250/0008; A61F 2250/006; A61F 2250/0062; A61F 2250/0091
USPC ........................................................ 623/6.48
See application file for complete search history.

(56) References Cited

U.S. PATENT DOCUMENTS

| | | | | |
|---|---|---|---|---|
| 4,657,546 A | * | 4/1987 | Shearing | A61F 2/1648 623/6.21 |
| 4,833,890 A | * | 5/1989 | Kelman | A61F 2/1613 623/6.17 |
| 4,878,910 A | * | 11/1989 | Koziol | A61F 2/1613 623/6.38 |
| 5,697,973 A | * | 12/1997 | Peyman | A61F 2/16 623/6.26 |
| 6,224,628 B1 | | 5/2001 | Callahan et al. | |
| 6,786,928 B2 | * | 9/2004 | Callahan | A61F 2/1613 623/6.18 |
| 8,398,709 B2 | * | 3/2013 | Ben Nun | A61F 2/1613 623/6.37 |
| 9,744,030 B2 | * | 8/2017 | Lee | A61F 2/1694 |
| 2002/0095212 A1 | * | 7/2002 | Boehm | A61F 2/1613 623/6.37 |
| 2003/0114927 A1 | * | 6/2003 | Nagamoto | A61F 2/1613 623/6.37 |
| 2006/0047339 A1 | * | 3/2006 | Brown | A61F 2/1602 623/6.13 |
| 2010/0204788 A1 | * | 8/2010 | Van Noy | A61F 2/1613 623/6.37 |
| 2011/0054600 A1 | * | 3/2011 | Bumbalough | A61F 2/1635 623/6.39 |
| 2011/0313521 A1 | * | 12/2011 | Angelopoulos | A61F 2/1694 623/6.43 |
| 2013/0281910 A1 | | 10/2013 | Tu | |

OTHER PUBLICATIONS

International Search Report and Written Opinion dated Mar. 17, 2017 in International Application No. PCT/US2016/57816.

* cited by examiner

INTRAOCULAR DEVICES AND METHODS FOR CORRECTION OF APHAKIA, RESTORATION OF ACCOMMODATION, AND TREATMENT OF GLAUCOMA

CROSS-REFERENCE TO RELATED APPLICATIONS

This application is a U.S. National phase filing under 35 U.S.C. § 371 of PCT/US2016/057816 (the "816 application") filed on Oct. 20, 2016 and entitled "INTRAOCULAR DEVICES AND METHODS FOR CORRECTION OF APHAKIA, RESTORATION OF ACCOMMODATION, AND TREATMENT OF GLAUCOMA." The '816 application claims priority from U.S. Provisional Application No. 62/244,260 filed on Oct. 21, 2015 and entitled "INTRAOCULAR DEVICES AND METHODS FOR CORRECTION OF APHAKIA, RESTORATION OF ACCOMMODATION, AND TREATMENT OF GLAUCOMA." Both of the aforementioned applications are incorporated herein by reference in their entirety for all purposes.

BACKGROUND

The present disclosure relates to intraocular devices and methods for correction of aphakia, restoration of accommodation, and treatment of glaucoma.

Glaucoma, characterized by an increase in intraocular pressure, is increasingly prevalent. According to the World Health Organization, glaucoma is the second leading cause of blindness in the world.

With increased age, or in some cases following cataract surgery, a congenital lens can become rigid, and a subject may thereby lose the ability to accommodate or focus up close even upon complete relation of the subject's anterior zonules, a condition known as farsightedness (hyperopia) or presbyopia.

Still other subjects, whether due to congenital defect, disease or injury, exhibit aphakia, and therefore require an intraocular lens, without which the subjects also exhibit refractive amblyopia.

Prior art devices and methods do not adequately address these ocular conditions, alone or in combination. The present disclosure addresses this need.

SUMMARY

An intraocular device according to the present disclosure comprises an implantable (e.g., injectable) prosthetic which can be placed in an eye before, at the time of, or following cataract surgery. In some embodiments, an example intraocular device can be placed in an eye solely for glaucoma, in which case no intraocular lens may be indicated.

In some embodiments, the device comprises a lens portion and a plurality of arms that radiate outward from the lens portion. The lens portion can comprise a central ring used to hold an intraocular lens. Each arm can comprise a foot plate which allows the device to push out distally against a ciliary body. This can have several effects. First, it can allow a stable and precise placement of the intraocular lens. Next, as the ciliary body relaxes and contracts with accommodative effort, movement of the arms can cause the intraocular lens to move forward and back, thus restoring the accommodative ability to the eye. This is typically lost after cataract surgery, as conventional intraocular lenses do not have the ability to move. And last, this counter-pressure on the ciliary body causes a decrease in aqueous production and a subsequent decrease in intraocular pressure.

BRIEF DESCRIPTION OF THE DRAWINGS

The accompanying drawings are included to provide a further understanding of the present disclosure and are incorporated in, and constitute a part of, this specification, illustrate various embodiments, and together with the description, serve to explain the principles of the disclosure.

DETAILED DESCRIPTION

The detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that logical, chemical, and mechanical changes may be made without departing from the spirit and scope of the disclosure. Thus, the detailed description herein is presented for purposes of illustration only and not of limitation.

For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected, coupled or the like may include permanent (e.g., integral), removable, temporary, partial, full, and/or any other possible attachment option. Additionally, any reference to without contact (or similar phrases) may also include reduced contact or minimal contact.

As used herein, "anterior" means directed toward or situated at the front or ventral, while "posterior" means directed toward or situated at the back or dorsal. The terms "proximal" and "distal," when used herein in relation to a device or device component, refer respectively, to directions closer to and farther away from the device's center. The embodiments described herein may be used in connection with not just humans, but also various organisms having mammalian anatomies.

The present disclosure generally provides an intraocular device, having a lens portion, and two or more arms. In a first example embodiment, and with reference to FIG. 1A, lens portion 110A is secured to a lens 160. Lens 160, in turn, can comprise a congenital lens or an intraocular lens. In another example embodiment, and with reference to FIG. 1B, lens portion 110B comprises an intraocular lens. Stated another way, in some embodiments, an intraocular lens can be separate from and clipped into (or otherwise secured to) an example device, as in FIG. 1A and described in greater detail infra. In other embodiments, however, an example device can have an intraocular lens built into it, as in FIG. 1B.

Figure 1A:
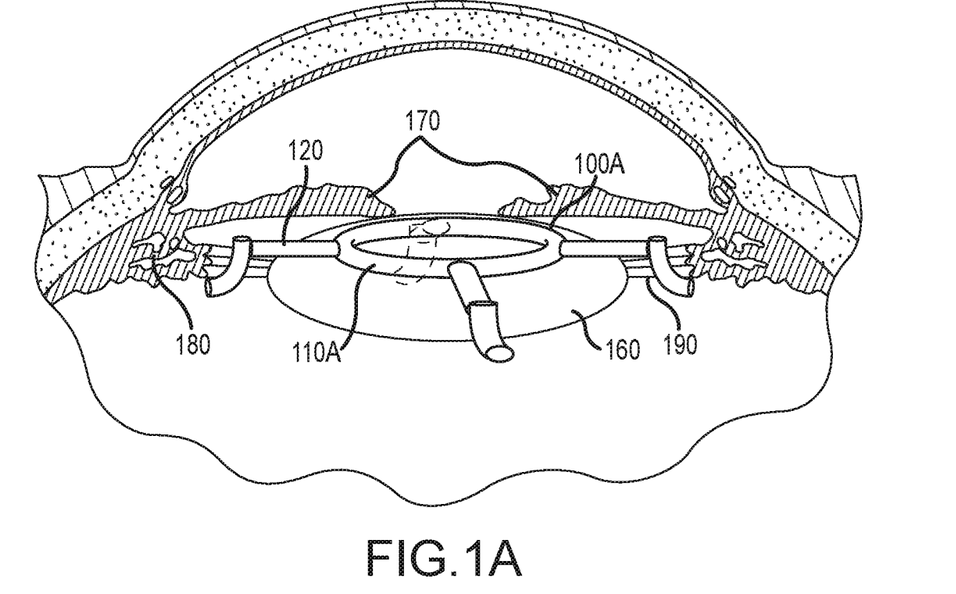
FIGS. 1A and 1B illustrate example intraocular devices placed in an eye in accordance with the present disclosure.
Figure 1B:
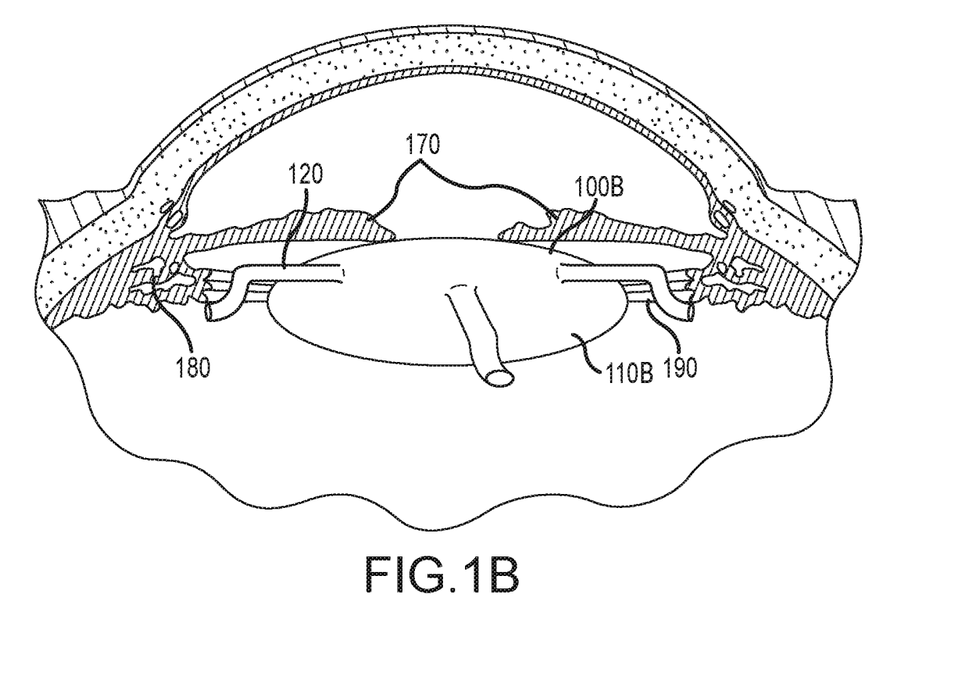
Figure 1C:
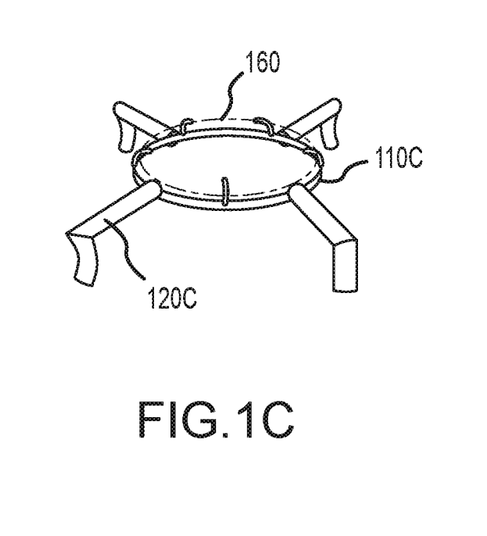
FIGS. 1C, 1D and 1E illustrate alternative views of example intraocular devices in accordance with the present disclosure.
Figure 1D:
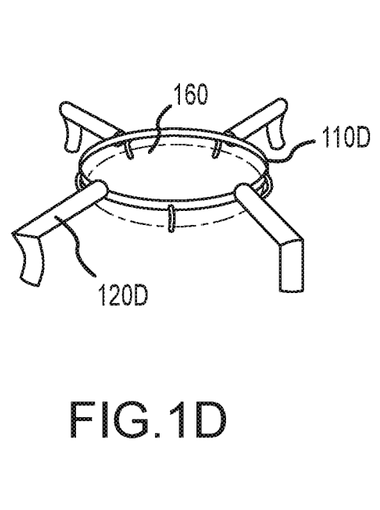

In various example embodiments, intraocular device 100A, 100B, is placed in an eye posterior to an iris 170. In an example embodiment, intraocular device 100A is placed in an eye anterior to lens 160, and between lens 160 and iris 170. However, in another example embodiment, intraocular device 100A is placed in an eye posterior to lens 160. In this regard, and with momentary reference to FIG. 1C, a lens 160 can be anterior to arms 120C and on an anterior side of a lens portion 110C. Similarly, and with reference to FIG. 1D, a lens 160 can be on a posterior side of a lens portion 110D, on the same side of lens portion 110D as arms 120D.

Figure 1E:
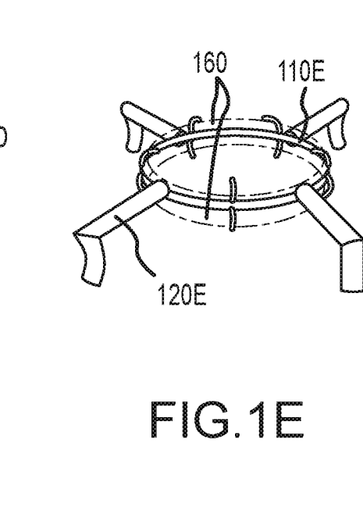

In still other embodiments, an example intraocular device comprises more than one lens (e.g., two intraocular lenses, or a congenital lens and an intraocular lens). In such embodiments, and with reference now to FIG. 1E, an intraocular device having a plurality of arms 120E can have a lens 160 on an anterior side of a lens portion 110E as well as a lens 160 on a posterior side of a lens portion 110E. This may have specific application to patients with end stage macular disease when an intraocular telescope may be indicated.

Turning back to FIGS. 1A and 1B, in various example embodiments, arms 120 of intraocular device 100 are at least in partial contact with a ciliary body 180. Moreover, in example embodiments, arms 120 of intraocular device 100 are adjacent or in-between one or more anterior zonules 190, for example, extending from a location that is anterior to one or more anterior zonules 190 in a posterior direction to a location that is posterior, and without affecting the integrity of the anterior zonules. The posteriorly directed foot plates can be placed between the radially oriented zonules with minimal disruption of capsular integrity. A portion of an example intraocular device (e.g., an arm, or a strut, hinge or foot plate of an arm) may be placed in the ciliary sulcus. An example intraocular device can be placed in the presence or absence of a lens capsule. In the presence of a lens capsule, an example intraocular device (or any portion thereof) can be attached to the lens capsule or a portion thereof. In various embodiments, intraocular device 100 can be useful in correction of aphakia, restoration of accommodation, and treatment of glaucoma.

As mentioned above, an intraocular device in accordance with the present disclosure comprises a lens portion. In some embodiments, and with reference back to FIG. 1B, the lens portion comprises, or is itself, an intraocular lens. In other embodiments, and with reference now to FIGS. 2A-2C, a lens portion 210 of an intraocular device 200, provides structural support and/or securement to a separate and distinct lens, for example, a congenital or an intraocular lens. In this regard, lens portion 210 can have a toroidal geometry. However, lens portion 210 can comprise other shapes as well including, but not limited to, profiles that are elliptical (e.g., circles, ovals, ellipses, and the like), non-elliptical (e.g., triangles, rectangles, squares, hexagons, trapezoids, pentagons, stars, and the like), or random. The dimensions of lens portion 210 can vary, but the diameter of an example lens portion is generally equal to or greater than the diameter of a subject's pupil in dim light, so as to minimize possible obstruction of the subject's field of vision. In some embodiments, the diameter of lens portion 210 is greater than that of a lens to be secured by lens portion 210. Depending on the subject, lens portion 210 can range from about 4.0 mm to about 12.0 mm, or about 8.0 mm.

The cross section A-A of lens portion 210 can likewise comprise various shapes, for example, as illustrated in FIGS. 2D-2G, showing, respectively, circle, oval, semi-circle and circle with shelf embodiments. In this regard, lens portion 210 can have a torus shape, but can also comprise other shapes including, but not limited to, profiles that are elliptical, non-elliptical, or random, as described supra. As an example, the cross section A-A of lens portion 210 can be made flatter and/or wider to act as an artificial iris in cases where needed.

Figure 3A:
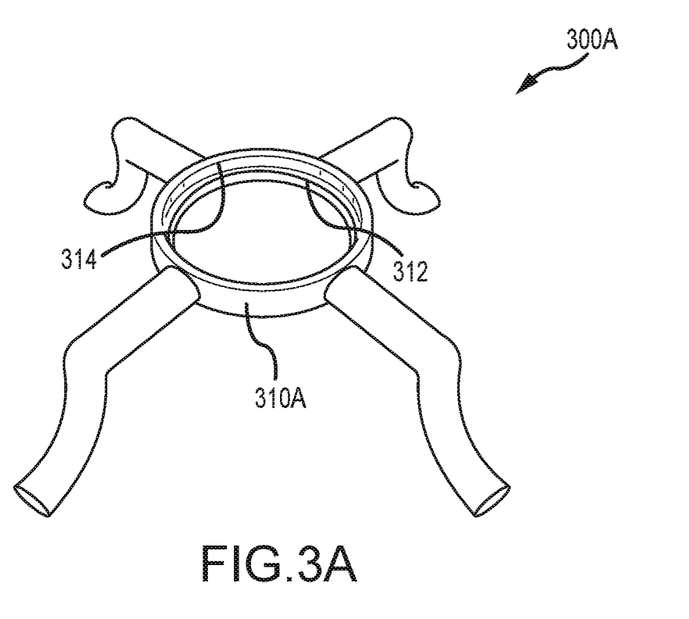
FIGS. 3A, 3B and 3C illustrate additional example intraocular devices in accordance with the present disclosure.

Moreover, the cross section A-A of lens portion 210 need not be consistent about the entirety of lens portion 210. For example, all or a portion of the perimeter of lens portion 210 can also have one or more recesses or grooves on a posterior surface to receive a lens. For example, and with momentary reference to FIG. 3A, a lens portion 310A of an intraocular device 300A in accordance with the present disclosure can comprise a shelf 312 to receive a lens, and a recess 314 to provide structural support and/or securement to a lens. Shelf 312 and recess 314 can extend partially or entirely about a perimeter of lens portion 310A, on an anterior and/or proximal surface of lens portion 310A. Shelf 312 and recess 314 can be on either the anterior or posterior face, or on both faces, of a lens portion of an example intraocular device.

Figure 3B:
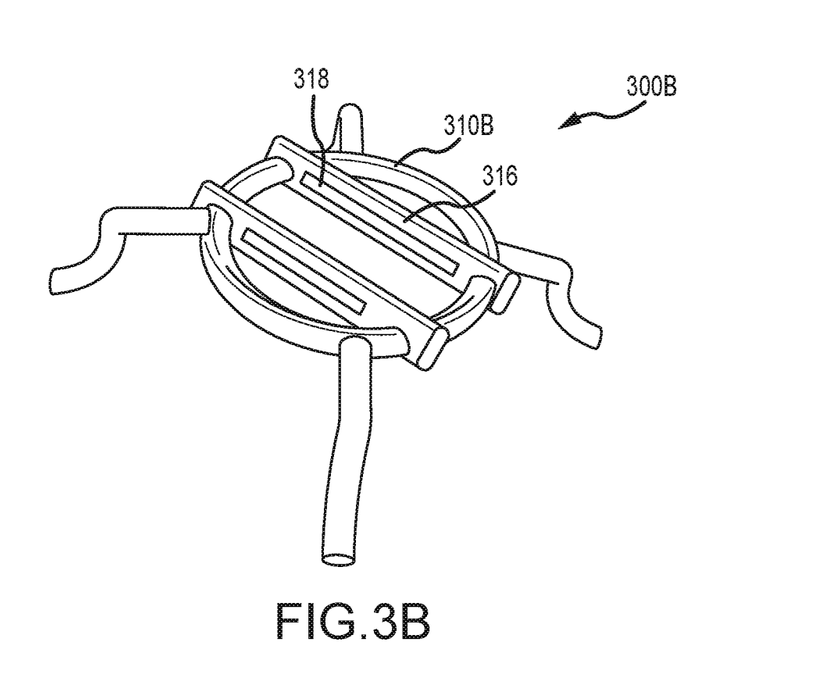

In other embodiments, and with reference to FIG. 3B, a lens portion 310B of an intraocular device 300B can comprise one or more (e.g., 2, 3, 4 or more) bars 316 spaced apart from one another and each extending across lens portion 310B. In turn, bars 316 can each have one or more openings 318 for receiving and providing structural support and/or securement to a lens, or a portion thereof (e.g., a haptic of an intraocular lens). In such embodiments, the lens may be smaller in diameter than that of lens portion 310B. Openings 318 can be aligned along a common plane, and/or aligned along the plane of lens portion 310B. Alternatively, openings 318 in some embodiments are not coplanar with the plane of lens portion 310B. Openings 318 can each also have one or more recesses or grooves on a posterior surface to receive a lens.

Figure 3C:
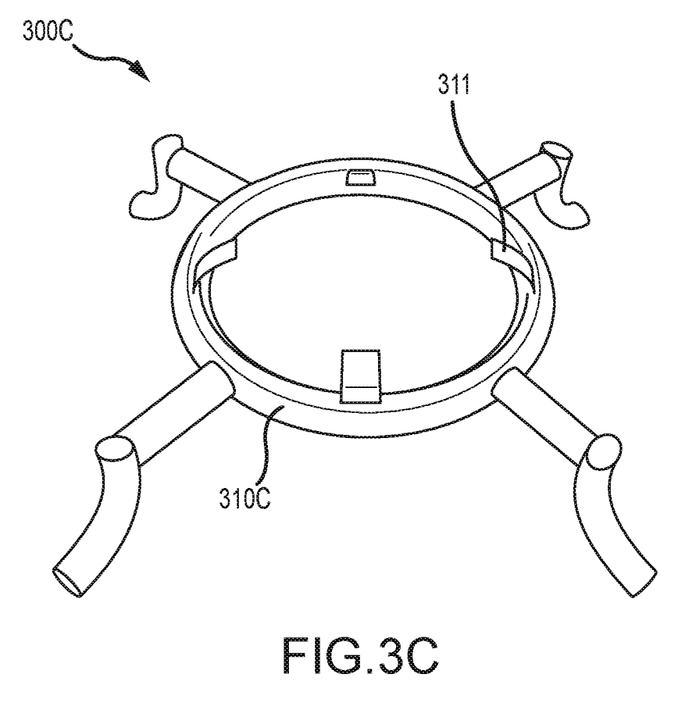

In yet other embodiments, an example intraocular device can comprise one or more sutures, clips or anchors to receive and provide structural support and/or securement of a lens portion to a lens. In addition, or in the alternative, one or more sutures, clips or anchors can secure an arm or a plurality of arms to a ciliary body. By way of example, a suture, clip or an anchor can be attached to a lens portion (on either the anterior or posterior face) and/or an arm. In this manner, the lens contained in an example intraocular device can be exchanged or removed at a later date if needed. With reference to FIG. 3C, a plurality of clips 311 can be attached to a lens portion 310C of an intraocular device 300C, wherein each clip 311 extends from lens portion 310C toward its center.

As discussed above, and with reference back now to FIGS. 2A-2C, an intraocular device 200 in accordance with the present disclosure can further comprise a plurality of arms 220. In an example embodiment, intraocular device 200 comprises two arms, three arms, four arms, five arms, six arms, seven arms, eight arms, nine arms, ten arms, 11-20 arms or more arms.

Figure 2A:
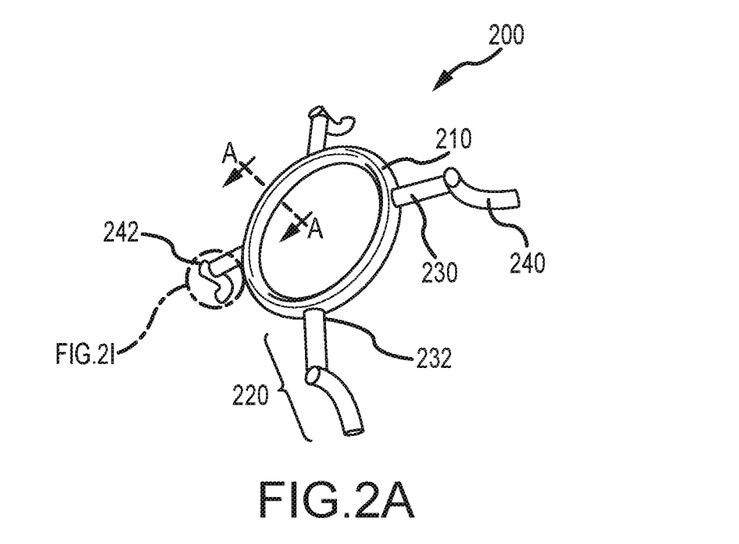
FIGS. 2A, 2B and 2C illustrate alternative views of another example intraocular device in accordance with the present disclosure.
Figure 2B:
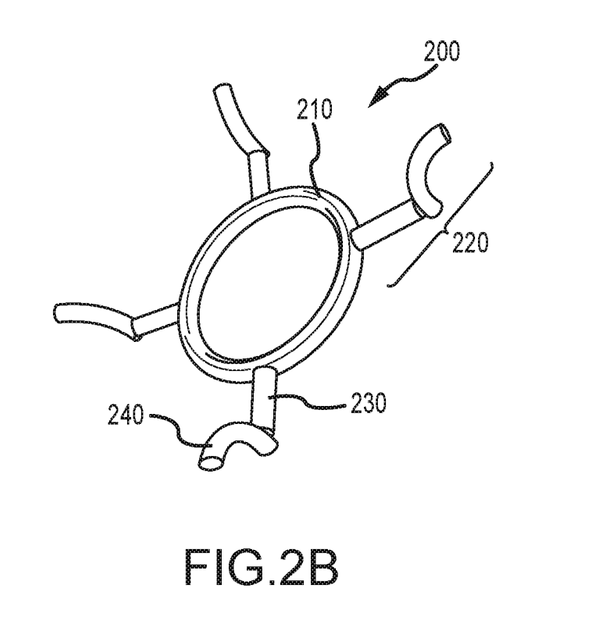
Figure 2C:
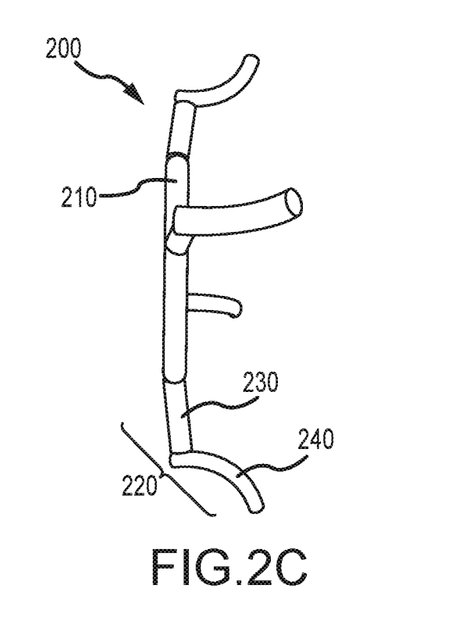
Figure 2D:
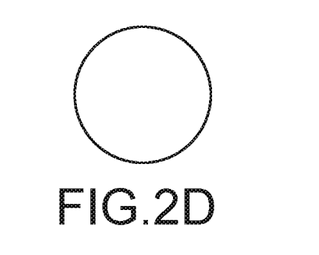
FIGS. 2D-2G illustrate cross sections of lens portions of example intraocular devices in accordance with the present disclosure.
Figure 2E:
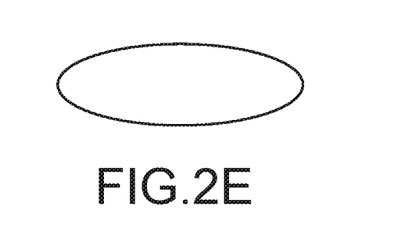
Figure 2F:
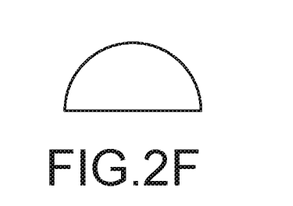
Figure 2G:
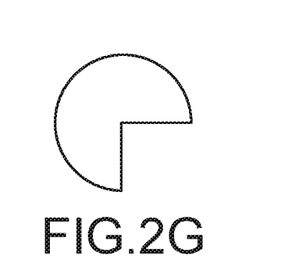
Figure 2H:
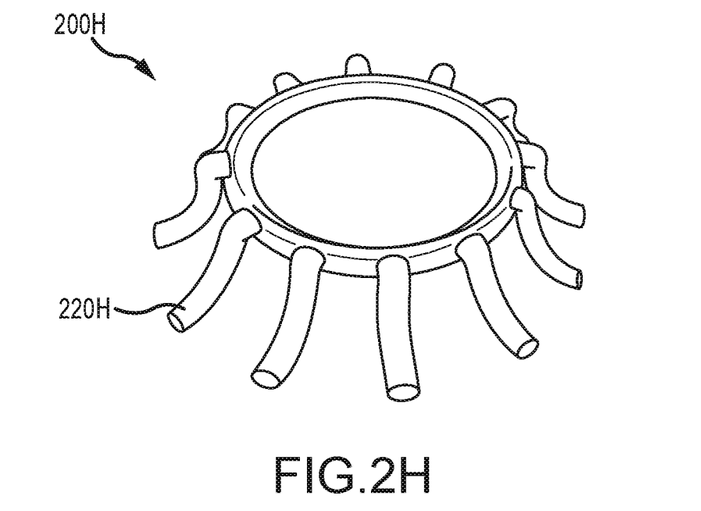
FIG. 2H illustrates an example intraocular device comprising a plurality of arms and having a generally frusto-conical shape.

With momentary reference to FIG. 2H, an example intraocular device 200H can comprise a plurality of arms 220H, wherein each arm 220H is concave in the anterior direction such that intraocular device 200H comprises a generally frustoconical shape.

In an example embodiment, arm 220 supports lens portion 210 and/or causes lens portion 210 to move when the ciliary body contracts or relaxes. Arm 220 is configured to translate a force from an end of arm 220 that is distal to lens portion 210 to a displacement at an end of arm 220 that is proximal and attached to lens portion 210.

In this manner, from the perspective of a single arm 220, the arm 220 can be configured to translate a ciliary body force in a first plane to displacement of a lens portion 210 in a second plane that is approximately normal to, or otherwise nonparallel with, the first plane.

From the perspective of the entire intraocular device 200, contraction of the ciliary body exerts opposing radially inward forces on each of the plurality of arms in a first plane, and wherein the forces displaces the lens portion in a second plane that is out of that plane (e.g., approximately normal to that plane).

In some embodiments, particularly comprising a congenital lens with intact anterior zonules, each of a plurality of arms 220 is an elongate element that is integral with, or separately attached to a perimeter of, lens portion 210. Plurality of arms 220 can be evenly spaced about the periphery of lens portion 210. Alternatively however, plurality of arms 220 can be unevenly spaced about the periphery of lens portion 210.

An arm 220 can comprise one or more linear, angled and/or curved portions (e.g., spherical, aspherical and/or sigmoidal). An arm 220 can also comprise one or more portions dimensioned (either larger or smaller) for contact with a ciliary body. In each of the foregoing, such portions can be coupled one to another, or integral one with another.

For example, in various embodiments, an arm 220 comprises a strut 230 coupled to a foot plate 240. In such embodiments, a proximal end of strut 230 is coupled to lens portion 210, and a distal end of strut 230 is coupled to a proximal end of foot plate 240. The proximal end of strut 230 may be coupled to lens portion 210 at a perimeter of lens portion 210, or in other suitable locations. When placed in vivo, at least a distal end of foot plate 240 is thus in contact with a ciliary body.

Strut 230 can be linear, angled and/or curved. Likewise, foot plate 240 can be linear, angled and/or curved. In various embodiments, however, strut 230 is linear while foot plate 240 is curved, for example, to conform with a ciliary body. The foot plate may rest on the anterior ciliary body, span it entirely, or contact any other portion of the ciliary body. Radius of curvature of foot plate 240 can vary, but in example embodiments is from about 0.2 mm to about 2 mm, or about 1 mm. Likewise, arc of foot plate 240 can vary, but can be from about 0 to about 180 degrees, or more preferably about 45 to about 90 degrees, or most preferably about 90 degrees in example embodiments. Foot plate 240 can be curved in a direction that is concave in the anterior direction as illustrated, or curved in a direction that is convex in the anterior direction.

Figure 2I:
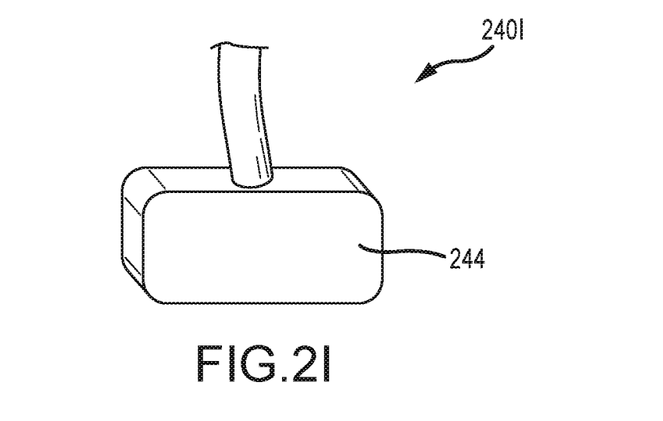
FIG. 2I illustrates a foot plate of an intraocular device having an increased ciliary body contact, in accordance with an embodiment of the present disclosure.

A distal end of foot plate 240, or a distal edge of foot plate 240 in contact with a ciliary body (e.g., inner edge of curve of foot plate 240), can comprise a flange, or a portion with an otherwise enlarged surface area relative to a proximal end of foot plate 240, or a proximal edge of foot plate 240, to provide for increased contact with the ciliary body (and increased compressing, occluding or damaging the ciliary epithelium, as discussed infra). For example, and with momentary reference to FIG. 2I, a foot plate 2401 can have an expanded portion 244 to provide for increased ciliary body contact.

Figure 2J:
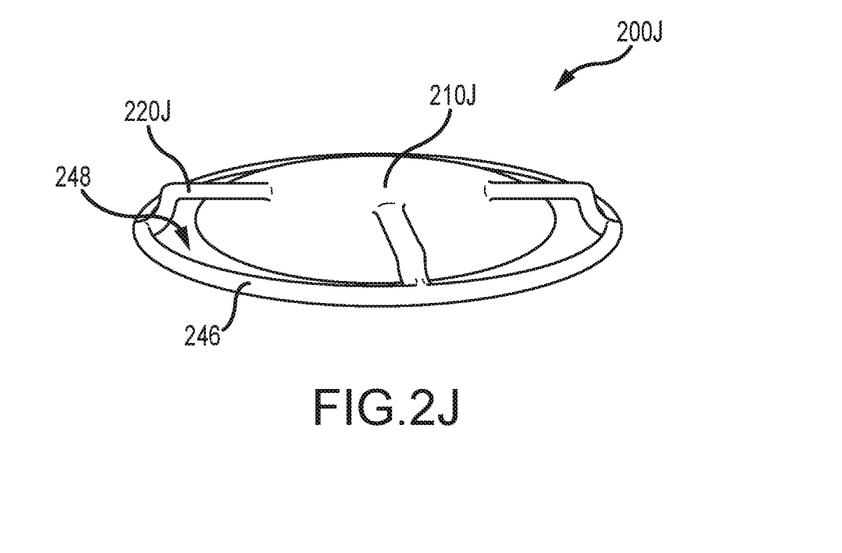
FIG. 2J illustrates an intraocular device having a continuous skirt, in accordance with an embodiment of the present disclosure.

In some embodiments, particularly comprising an intraocular lens lacking any anterior zonules, an intraocular device of the present disclosure can comprise a continuous or substantially continuous skirt extending radially from a perimeter of a lens portion. The skirt can be in place of, or in addition to, the plurality of arms, and give the device a frustoconical shape. For example, and with momentary reference to FIG. 2J, an example intraocular device 200J can comprise a lens portion 210J that is an intraocular lens, a plurality of arms 220J, and a continuous skirt 246, wherein a plurality of open portions 248 are disposed between plurality of arms 220J and continuous skirt 246. In other embodiments, intraocular device 200J does not comprise open portions 248. That is, rather than having open portions or windows between arms, intraocular device 200J can comprise a continuous surface extending from continuous skirt 246 to a lens 210J (or a lens portion, as applicable) thus having a generally frustoconical shape. In still other embodiments, intraocular device 200J, in lieu of a lens portion 210J, comprises a lens portion 210 (with reference to FIGS. 2A-2C) that supports a congenital lens or an intraocular lens.

In some embodiments, a portion of an intraocular device as described herein comprises a flexible or resilient material to facilitate a force in a plane being translated into a displacement out of the plane (e.g., a normal plane), as discussed supra. Further, the material may be made of transparent material, such as intraocular lenses, that does not block transmission of light. In some embodiments, the lens portion of an intraocular device as described herein is compatible with laser transmission and adjustment.

Elements of the present disclosure generally comprise biocompatible, immunologically inert materials, for example, acrylic, polypropylene (e.g., size 5-0), polymethyl methacrylate (PMMA), silicone, shape memory alloys such as nitinol and shape memory polymers, polyvinylidene difluoride (PVDF), stainless surgical steel, and Collamer® (STAAR Surgical Company). Elements of the present disclosure may be completely or semi-transparent or translucent to allow the passage of light. Different elements of the present disclosure need not necessarily comprise the same material.

Figure 2K:
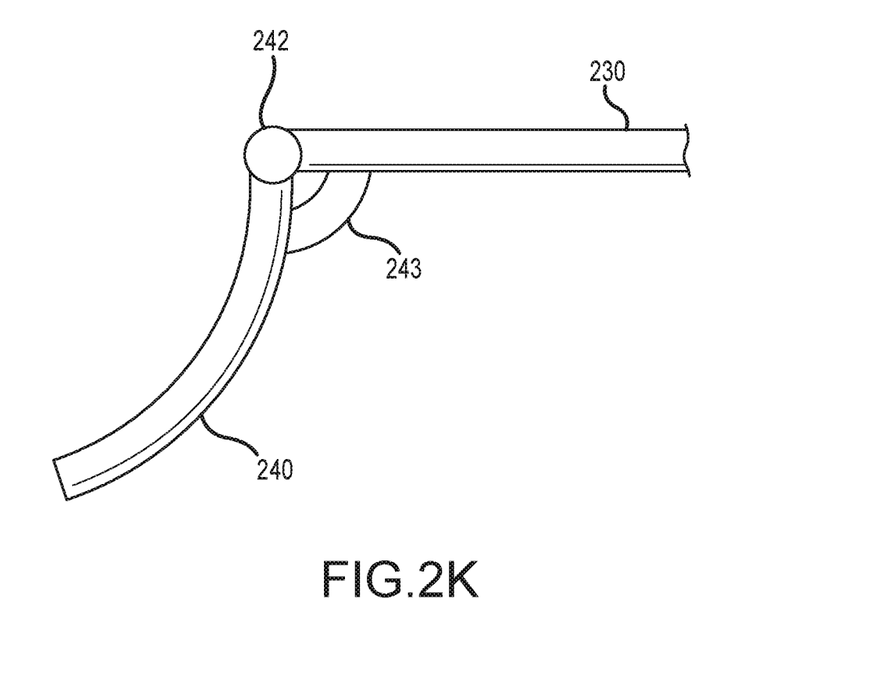
FIG. 2K illustrates a blown up portion of FIG. 2A.

Intraocular device 200 in accordance with the present disclosure can also comprise one or more hinges, for example, between lens portion 210 and strut 230 at an intersection 232, and/or between foot plate 240 and strut 230 at an intersection 242. In an example, embodiment, and with reference to FIGS. 2A and 2K, each intersection 242 of intraocular device 200 can comprise a fulcrum or hinge 242 between strut 230 and foot plate 240, and comprise a plurality of levers 243 extending between strut 230 and foot plate 240. In this manner, a force in a plane can be translated into a displacement out of the plane.

A hinge is generally any structure or lack thereof that facilitates movement of one element with respect to another. In this regard, a hinge can be a weakened portion, or can be a hinge or joint known by persons skilled in the art or hereafter discovered, for example, a pivot hinge, or a ball and socket joint. In some embodiments, particularly in embodiments comprising a rigid intraocular device, a hinge may facilitate a force in a plane being translated into a displacement out of the plane (e.g., a normal plane), as discussed supra. In some embodiments, a hinge can be configured to transfer a horizontal force of the ciliary body into a vertical movement of the lens. In some embodiments, a hinge can provide conformability for movement and growth, and/or may facilitate delivery of intraocular device 200 to a treatment site.

Each of the lens portion, arm, strut and foot plate can be temporarily or permanently coupled to one or more of the others by adhesion, compression fit, threading, suture, glue, thermal bonding, nitinol or other shape memory clips, and the like. In example embodiments, a coupling is configured to maintain coupled elements firmly in place relative to one another even when subjected to shaking and acceleration/deceleration movements.

Any element of the present disclosure can be coated with or otherwise comprise a therapeutic agent, such as a drug, antiproliferative, antithrombotic, etc.

Any portion of an intraocular device as described herein can comprise a radio-opaque or echogenic element (e.g., markers or bands) that enhances imaging or detection during and/or following placement. Such elements can be comprised of one or more of tungsten, gold, platinum and the like.

An example intraocular device can comprise one or more features to direct and/or maintain a desired rotational orientation of the intraocular device in vivo. For example, an example intraocular device can comprise one or more weighted portions, or one or more arms that differ in length from the remaining arms.

The present disclosure also comprises various methods for correction of aphakia, restoration of accommodation, and treatment of glaucoma. Without limiting the foregoing, an example intraocular device can be placed in aphakic, pseudophakic, or phakic eyes for both refractive and/or glaucoma treatment. In the case of phakic eyes, the intraocular device may rest anterior to the anterior capsule of the native crystalline lens. Still other indications include phacodonesis or pseudophacodonesis, where the lens in the eye is unstable.

Figure 2L:
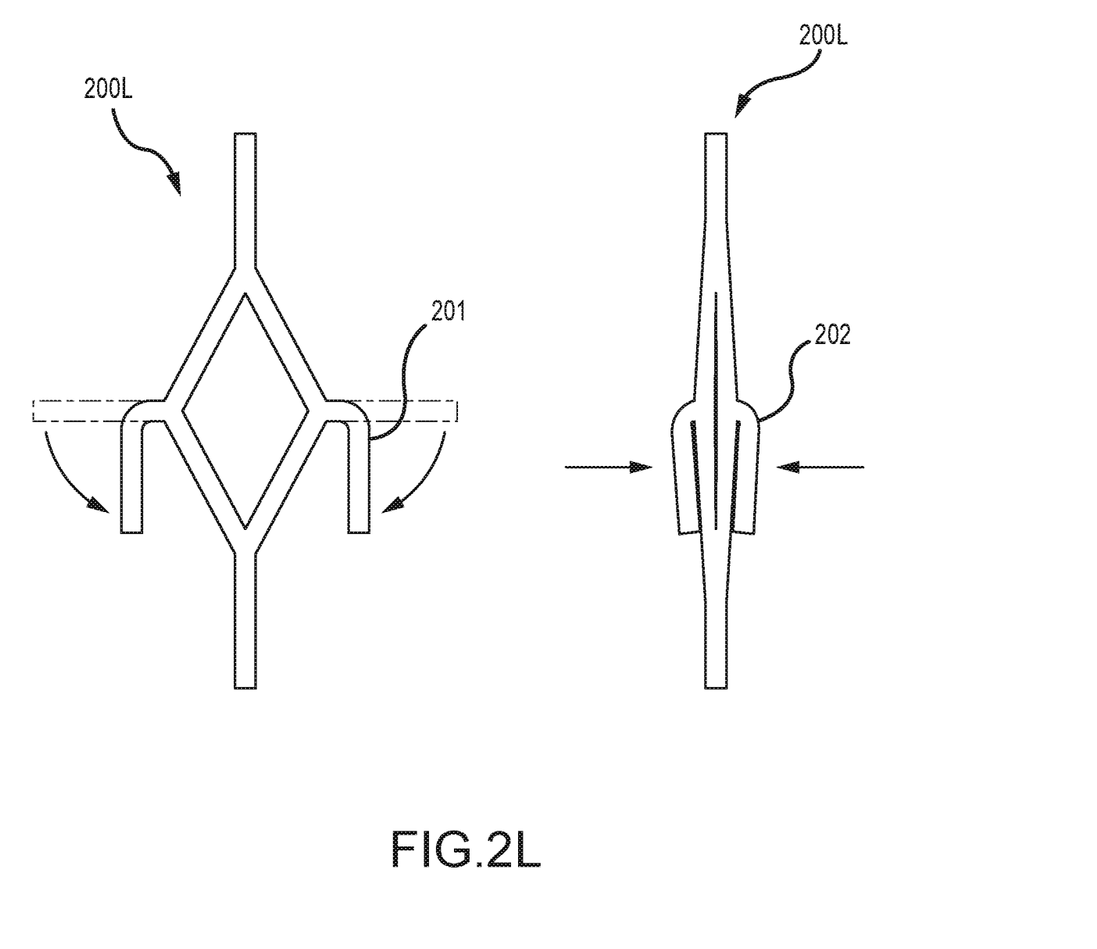
FIG. 2L illustrates an intraocular device in accordance with the present disclosure, comprising partially folded and fully folded configurations.

In an example method of delivery, an intraocular device is configured to be folded, rolled or otherwise compressed (e.g., to a diameter of about 3 mm or less) so as to be delivered to a treatment site as an injectable device. For example, and with momentary reference to FIG. 2L, an example intraocular device 200L can have a partially folded configuration 201, and a fully folded configuration 202. By way of non-limiting examples, intraocular device 200L can comprise one or more hinges as described supra, or be comprised of a resilient material (e.g., a polymer such as polypropylene or a shape memory alloy such as nitinol) to accommodate folding or rolling.

Example treatment methods are disclosed. In some embodiments, an intraocular device can be placed in an eye posterior to a lens. In such embodiments, a strut of an arm can extend distally from a lens portion, and a foot plate of the arm can extend anteriorly from the strut to be at least in partial contact with a ciliary body, and adjacent or in between one or more anterior zonules.

Figure 4A:
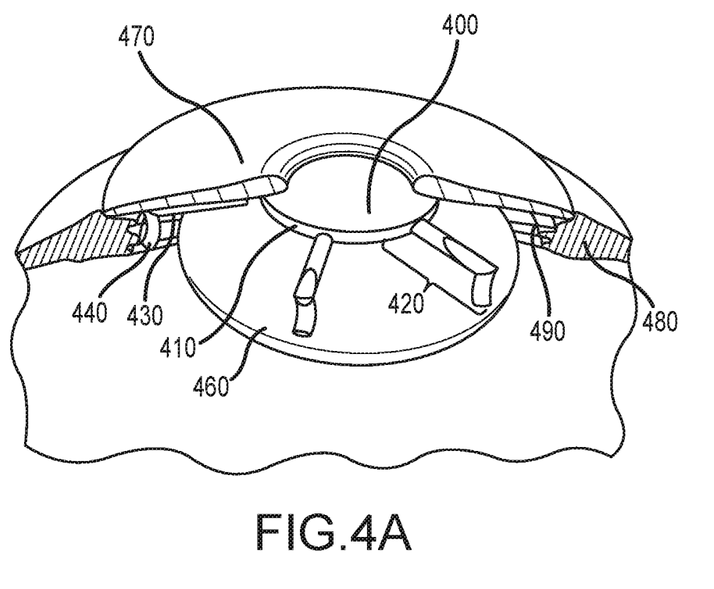
FIGS. 4A and 4B illustrate perspective and side views respectively, of an example intraocular device placed in an eye in accordance with the present disclosure.
Figure 4B:
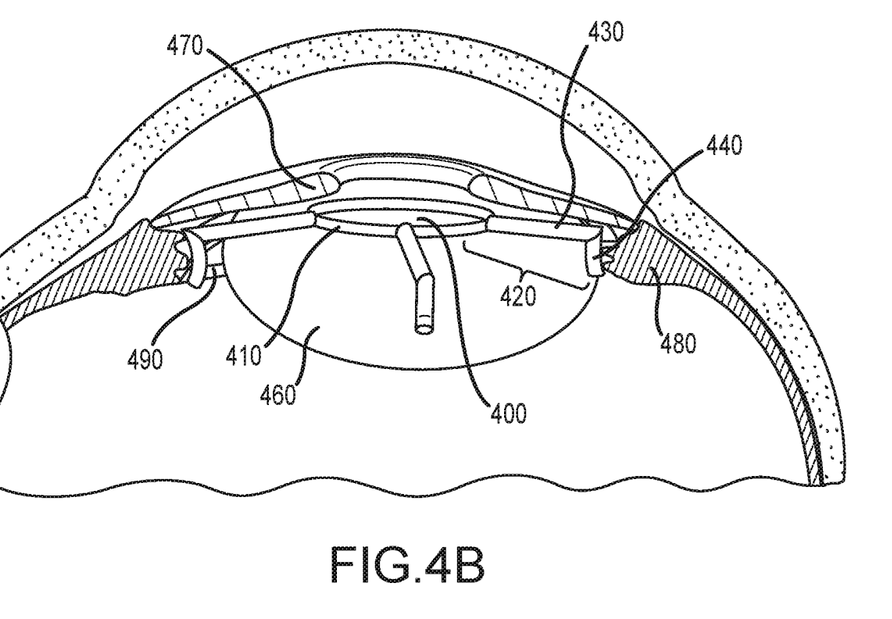

In other embodiments, however, and with reference now to FIGS. 4A and 4B, intraocular device 400 can be placed in an eye anterior to a lens 460 and posterior to an iris 470. In such embodiments, strut 430 of arm 420 can extend distally from lens portion 410, and foot plate 440 of arm 420 can extend posteriorly from strut 430 to be at least in partial contact with a ciliary body 480, and adjacent or in between one or more anterior zonules 490. In turn, lens portion 410 of intraocular device 400 can comprise, or be secured to, a lens 460, whether a congenital or an intraocular lens.

Foot plate 440 being in contact with, and/or foot plate 440 exerting a force on or displacement to, ciliary body 480 can decrease the production of aqueous fluid (e.g., by compressing, occluding or damaging the ciliary epithelium) and thereby lower intraocular pressure, for example, as a therapeutic device to treat glaucoma. Decreasing the production of aqueous fluid and thereby lowering intraocular pressure in an eye comprising ciliary body 480 can be achieved in a predictable manner by adjusting the profile of foot plate 440 to be larger of smaller, or made more or less sharp or otherwise invasive. For example, a larger, more sharp foot plate may lower intraocular pressure more than a smaller, less sharp foot plate. In example, embodiments, one or more foot plates can have cleats, or small raised areas, that promote traction or grasp on the ciliary body.

The amount of pressure that is applied to the ciliary body can be titrated by sizing the foot-plate to foot-plate length of the device. For purely refractive applications, this pressure may be just enough to transmit the accommodative forces from the ciliary body to the device, with no effect on aqueous production. In purely glaucomatous applications, it may be desirable to have the force sufficiently high to decrease the production of aqueous, with minimal change on transmission of accommodative forces.

In this regard, example embodiments comprise decreasing the intraocular pressure within the anterior chamber by about 1 mmHg to about 15 mmHg, or more in severe cases. In this manner, the intraocular pressure within the anterior chamber can be controllably adjusted to less than about 16 mmHg, more preferably less than about 14 mmHg, most preferably about 10 mmHg, or an otherwise normal or improved intraocular pressure. Example embodiments still further comprise decreasing the intraocular pressure within the anterior chamber for at least about 2 weeks, or at least about 3-6 months, or at least about 1 year or more, or permanently. In example embodiments, the desired amount of intraocular pressure reduction can be augmented by choosing the size of an example intraocular device, and/or a plurality of intraocular devices.

In addition, contraction and relaxation of ciliary body 480 can facilitate anterior and posterior movement respectively, of lens portion 410. More precisely, a force associated with contraction and relaxation of ciliary body 480 can be translated through the plurality of arms 420 as described supra, for example, as a therapeutic device to accommodate or focus up close and thereby treat presbyopia. More specifically, the plurality of arms can provide a mechanical advantage, translating the radial movement of the ciliary body into an anterior/posterior movement of a congenital or an intraocular lens. In addition to changing the direction of the movement, the translation can change the magnitude of the movement. Thus, intraocular device 400 is configured, upon contraction and relaxation of ciliary body 480, to displace a lens portion anteriorly and posteriorly at least about 0.2 mm, more preferably at least about 0.5 mm, most preferably at least about 1.0 mm.

In various example embodiments, an intraocular device in accordance with the present disclosure can be injected months to years after cataract surgery and IOL placement, wherein the posterior aspect of the intraocular device's lens portion (e.g., a ring) can clip onto the front aspect of the IOL and pull the IOL forward with accommodation.

Subluxation testing was performed in connection with the present disclosure. A control group demonstrated subluxation of the crystalline lens when placed for 2 min on a standard plate agitator on the high setting. By contrast, a group implanted with an intraocular device in accordance with the present disclosure demonstrated no subluxation of lens or implant.

In another subluxation test, the amount of centripetal force required to dislocate a lens was measured for fresh pig eyes having the cornea and iris excised to expose the anterior capsule. The test was conducted with and without an intraocular device in accordance with the present disclosure, the fresh pig eyes having varying degrees of zonular rupture (taking care to avoid the lens capsule). The results are shown in Table 1 below, and demonstrate the efficacy of the present disclosure.

TABLE 1

|  | Degrees of zonular rupture | Rotations per second | Subluxation | n value |
| --- | --- | --- | --- | --- |
| No intraocular device | 0 | 9 | No | n = 5 |
|  | 90 | 9 | Yes | n = 5 |
|  | 180 | 7 | Yes | n = 5 |
|  | 270 | 6 | Yes | n = 5 |
| Intraocular device | 0 | 9 | No | n = 5 |
|  | 90 | 9 | No | n = 5 |
|  | 180 | 9 | No | n = 5 |
|  | 270 | 9 | No | n = 5 |

It will be apparent to those skilled in the art that various modifications and variations can be made in the present disclosure without departing from the spirit or scope of the disclosure. For example, while the present disclosure has been described with reference to supporting a congenital lens or an intraocular lens, an example intraocular device can be used to support additional implements, such as wireless intraocular pressure and/or aqueous glucose content measurement systems, as well as sustained drug delivery systems. Thus, it is intended that the embodiments described herein cover the modifications and variations of this disclosure provided they come within the scope of the appended claims and their equivalents.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

We claim:

1. An intraocular device comprising:
  a lens portion configured to support a separate and distinct lens; and
  a plurality of arms radiating distally from the lens portion, wherein the plurality of arms are integral with the lens portion,
  wherein each of the plurality of arms comprises a strut and a foot plate,
  wherein the foot plate is curved to conform with a ciliary body, and
  wherein the intraocular device further comprises a hinge lever extending between the strut and the footplate of each of the plurality of arms.

2. The intraocular device of claim 1 wherein the lens portion comprises a shelf, a recess, a bar, or a clip configured to support the separate and distinct lens.

3. The intraocular device of claim 1 wherein the hinge lever is configured to facilitate translation of force from along a first plane to along a second plane non-parallel with the first plane.

4. The intraocular device of claim 1, wherein the plurality of arms are evenly spaced about, and extend radially outward from, a periphery of the lens portion such that gaps are defined between adjacent arms of the plurality of arms.

5. The intraocular device of claim 1 wherein the strut is linear, wherein the strut is coplanar with the lens portion.

6. The intraocular device of claim 5 wherein the foot plate is concave in an anterior direction.

7. The intraocular device of claim 6 wherein contraction of the ciliary body exerts a force on each of the plurality of arms in a first direction along a first plane, and wherein the force displaces the lens portion in a second direction along a second plane.

8. The intraocular device of claim 7 wherein the first plane is normal to the second plane.

9. The intraocular device of claim 6 wherein the foot plate is configured to contact the ciliary body to provide a decrease in the production of aqueous fluid.

10. The intraocular device of claim 9 wherein the foot plate comprises a distal edge, wherein the decrease in the production of aqueous fluid, in response to the distal edge of the foot plate contacting the ciliary body, lowers an intraocular pressure in an eye comprising the ciliary body.

11. A method for treating an ocular condition comprising:
  providing an intraocular device, wherein the intraocular device comprises a lens portion, and a plurality of arms radiating distally from the lens portion, wherein the plurality of arms are integral with the lens portion, wherein each of the plurality of arms comprises a strut and a foot plate, and wherein the foot plate is curved to conform with a ciliary body;
  placing the intraocular device in a subject exhibiting presbyopia or glaucoma; and
  securing a separate and distinct lens to the lens portion of the intraocular device;
  wherein placing the intraocular device in the subject comprises positioning the foot plate such that it contacts the ciliary body to provide a decrease in the production of aqueous fluid.

12. The method for treating an ocular condition of claim 11 wherein contraction of the ciliary body exerts a force on each of the plurality of arms in a first plane, and wherein the force displaces the lens portion in a second plane and thereby treats presbyopia.

13. The method for treating an ocular condition of claim 12 wherein the first plane is normal to the second plane.

14. The method for treating an ocular condition of claim 11, wherein placing the intraocular device comprises lowering an intraocular pressure in an eye comprising the ciliary body.

15. The intraocular device of claim 1, wherein a radius of curvature of the curved foot plate is between 0.2 mm and 2.0 mm.

16. The intraocular device of claim 1, wherein an arc of the curved foot plate is between about 45 degrees to about 90 degrees.

17. An intraocular device comprising:
- a lens portion configured to support a separate and distinct lens; and
- a plurality of arms radiating distally from the lens portion, wherein the plurality of arms are integral with the lens portion,
- wherein each of the plurality of arms comprises a strut and a foot plate,
- wherein the foot plate is curved to conform with a ciliary body, and
- wherein a radius of curvature of the curved foot plate is between 0.2 mm and 2.0 mm.

\* \* \* \* \*